United States Patent
Fiser et al.

(10) Patent No.: US 12,390,541 B2
(45) Date of Patent: Aug. 19, 2025

(54) MUTANT VARIANTS OF PD-1 RECEPTOR WITH SELECTIVE BINDING TO PD-L1 AND USES THEREOF

(71) Applicant: Albert Einstein College of Medicine, Bronx, NY (US)

(72) Inventors: Andras Fiser, New York, NY (US); Rojan Shrestha, Bronx, NY (US); Steven C. Almo, Pelham, NY (US); Sarah C. Garrett, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 1155 days.

(21) Appl. No.: 17/278,869

(22) PCT Filed: Sep. 18, 2019

(86) PCT No.: PCT/US2019/051640
§ 371 (c)(1),
(2) Date: Mar. 23, 2021

(87) PCT Pub. No.: WO2020/068500
PCT Pub. Date: Apr. 2, 2020

(65) Prior Publication Data
US 2022/0047729 A1 Feb. 17, 2022

Related U.S. Application Data

(60) Provisional application No. 62/736,477, filed on Sep. 26, 2018.

(51) Int. Cl.
*A61K 51/08* (2006.01)
*C07K 14/705* (2006.01)

(52) U.S. Cl.
CPC ........ *A61K 51/08* (2013.01); *C07K 14/70532* (2013.01); *C07K 2319/30* (2013.01)

(58) Field of Classification Search
None
See application file for complete search history.

(56) References Cited

U.S. PATENT DOCUMENTS

2006/0105413 A1    5/2006  Nunez et al.
2017/0233451 A1 *  8/2017  Ring .................. A61K 35/17
                                                424/1.41

FOREIGN PATENT DOCUMENTS

WO       2003/022875 A2      3/2003
WO    WO-2016164428 A1 *   10/2016  ......... A61K 38/1774
WO    WO-2018077189 A1 *    5/2018  ............. A61K 38/17

OTHER PUBLICATIONS

Li et al (Cancer Science, Jun. 2018, 109:2435-2445).*
English translation of WO 2018077189, Li et al, published May 3, 2018.*
Maute et al., "Engineering high-affinity PD-1 variants for optimized immunotherapy and immuno-PET imaging", PNAS, 2015, E6506-E6514.
Shrestha et al., "Computational Redesign of PD-1 Interface for PD-L1 Ligand Selectivity", Structure, 2019, 27(5): 829-836.e3.

* cited by examiner

*Primary Examiner* — Laura B Goddard
(74) *Attorney, Agent, or Firm* — Fox Rothschild LLP

(57) ABSTRACT

Disclosed are human Programmed Cell Death-1 (PD-1) receptor mutants having selectivity for PD-L1 compared to PD-L2, methods of obtaining the mutants, and uses of the mutants for treatment and imaging.

Figure 2A:
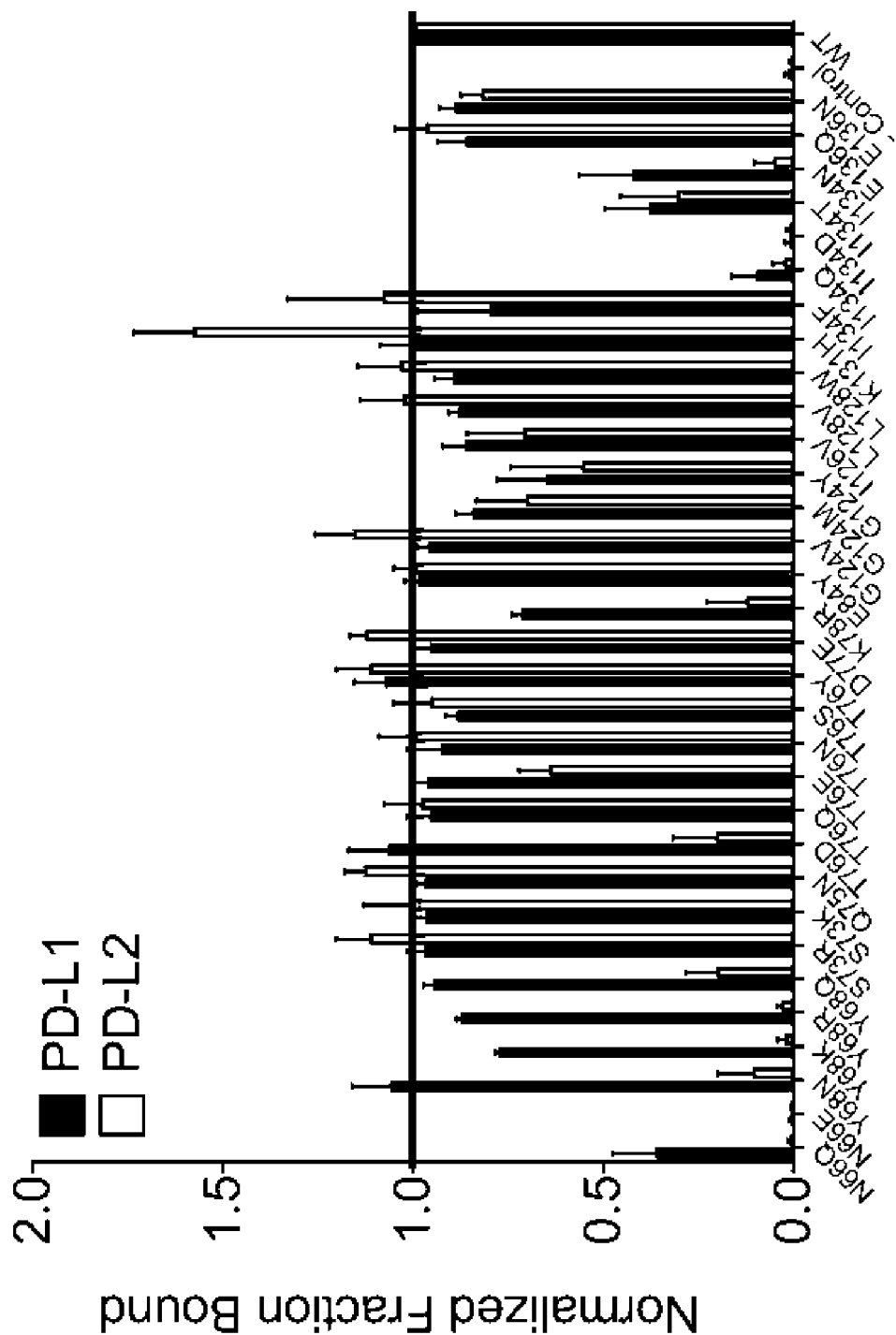

12 Claims, 5 Drawing Sheets
Specification includes a Sequence Listing.

(A)
```
hPD-1  33  NPPTFSPALLVVTEGDNATFTCSFSNTSESFVLNWYRMSPSNQTDKLAAFP---EDRSQPGQDCRFRVTQL  100
mPD-1   -  -SLTFYPAWLTVSEGANATFTCSLSNWSEDLMLNWNRLSPSNQTEKQAAFCNGLSQPV---QDARFQIIQL   90
```
```
hPD-1  101 PNGRDFHMSVVRARRNDSGTYLCGAISLAPKAQIKESLRAELRVTERRA             140
mPD-1   91 PNRHDFHMNILDTRRNDSGIYLCGAISLHPKAKIEESPGAELVVTE---
```

(B)
```
hPD-L1  20  LFTVTVPKELYIIEHGSNVTLECNFDTGSHVNLGAITASLQKVENDTSPHRERATLLEEQLPLGKASFHIP   90
mPD-L2  18  LFTVTAPKEVYTVDVGSSVSLECDFDRRECTELEGIRASLQKVENDTSLQSERATLLEEQLPLGKALFHIP
```
```
hPD-L1  91  QVQVRDEGQYQCIIIYGVAWDYKYLTVKVK                                       120
mPD-L2      SVQVRDSGQYRCLVICGAAWDYKYLTLKVK
```

(C)
```
hPD-L1  18  AFTVTVPKDLYVVEYGSNMTIECKFPVEKQLDLAALIVYWEME----DKNIIQFVHGEEDLKVQHSSYRQR   80
hPD-L2  18  LFTVTVPKELYIIEHGSNVTLECNFDTGSHVNLGAITASLQKVENDTSPHR------------------ER
```
```
hPD-L1  85  ARLLKDQLSLGNAALQITDVKLQDAGVYRCMISYG-GADYKRITVKVN                     130
hPD-L2      ATLLEEQLPLGKASFHIPQVQVRDEGQYQCIIIYGVAWDYKYLTLKVK
```

FIG. 1A-1C

SEQUENCE LISTING

```
<160> NUMBER OF SEQ ID NOS: 33

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
```

```
                    245                 250                 255
Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 2
<211> LENGTH: 117
<212> TYPE: PRT
<213> ORGANISM: Homo sapiens

<400> SEQUENCE: 2

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Cys Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Ala Gln Ile Lys Glu Ser Leu Arg Ala Glu Leu Arg Val
            100                 105                 110

Thr Glu Arg Arg Ala
        115

<210> SEQ ID NO 3
<211> LENGTH: 114
<212> TYPE: PRT
<213> ORGANISM: Mus musculus

<400> SEQUENCE: 3

Ser Leu Thr Phe Tyr Pro Ala Thr Arg Leu Thr Val Ser Glu Gly Ala
1               5                   10                  15

Asn Ala Thr Phe Thr Cys Ser Leu Ser Asn Trp Ser Glu Asp Leu Met
            20                  25                  30

Leu Asn Trp Asn Arg Leu Ser Pro Ser Asn Gln Thr Glu Lys Gln Ala
        35                  40                  45

Ala Phe Ser Asn Gly Leu Ser Gln Pro Val Gln Asp Ala Arg Phe Gln
    50                  55                  60

Ile Ile Gln Leu Pro Asn Arg His Asp Phe His Met Asn Ile Leu Asp
65                  70                  75                  80

Thr Arg Arg Asn Asp Ser Gly Ile Tyr Leu Cys Gly Ala Ile Ser Leu
                85                  90                  95

His Pro Lys Ala Lys Ile Glu Ser Pro Gly Ala Glu Leu Val Val
            100                 105                 110

Thr Glu

<210> SEQ ID NO 4
<211> LENGTH: 101
<212> TYPE: PRT
<213> ORGANISM: Homo sapiens

<400> SEQUENCE: 4
```

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys
            100

<210> SEQ ID NO 5
<211> LENGTH: 102
<212> TYPE: PRT
<213> ORGANISM: Mus musculus

<400> SEQUENCE: 5

Leu Phe Thr Val Thr Ala Pro Lys Glu Val Tyr Thr Val Asp Val Gly
1               5                   10                  15

Ser Ser Val Ser Leu Glu Cys Asp Phe Asp Arg Arg Glu Cys Thr Glu
            20                  25                  30

Leu Glu Gly Ile Ile Arg Ala Ser Leu Gln Lys Val Glu Asn Asp Thr
        35                  40                  45

Ser Leu Gln Ser Glu Arg Ala Thr Leu Leu Glu Glu Gln Leu Pro Leu
    50                  55                  60

Gly Lys Ala Leu Phe His Ile Pro Ser Val Gln Val Arg Asp Ser Gly
65                  70                  75                  80

Gln Tyr Arg Cys Leu Val Ile Cys Gly Ala Ala Trp Asp Tyr Lys Tyr
                85                  90                  95

Leu Thr Val Lys Val Lys
            100

<210> SEQ ID NO 6
<211> LENGTH: 114
<212> TYPE: PRT
<213> ORGANISM: Homo sapiens

<400> SEQUENCE: 6

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
                100                 105                 110

Val Asn

<210> SEQ ID NO 7
<211> LENGTH: 101
<212> TYPE: PRT
<213> ORGANISM: Mus musculus

<400> SEQUENCE: 7

```
Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys
            100
```

<210> SEQ ID NO 8
<211> LENGTH: 8
<212> TYPE: PRT
<213> ORGANISM: Artificial Sequence
<220> FEATURE:
<223> OTHER INFORMATION: rs-pharmacophore

<400> SEQUENCE: 8

```
Asp Glu Pro Asn Gln Arg His Thr
1               5
```

<210> SEQ ID NO 9
<211> LENGTH: 7
<212> TYPE: PRT
<213> ORGANISM: Artificial Sequence
<220> FEATURE:
<223> OTHER INFORMATION: rs-pharmacophore

<400> SEQUENCE: 9

```
His Lys Asn Gln Arg Thr Trp
1               5
```

<210> SEQ ID NO 10
<211> LENGTH: 5
<212> TYPE: PRT
<213> ORGANISM: Artificial Sequence
<220> FEATURE:
<223> OTHER INFORMATION: rs-pharmacophore

<400> SEQUENCE: 10

```
His Lys Asn Gln Trp
1               5
```

<210> SEQ ID NO 11
<211> LENGTH: 7
<212> TYPE: PRT
<213> ORGANISM: Artificial Sequence
<220> FEATURE:
<223> OTHER INFORMATION: rs-pharmacophore

<400> SEQUENCE: 11

His Lys Asn Gln Arg Trp Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: rs-pharmacophore

<400> SEQUENCE: 12

His Lys Asn Gln Arg Trp Tyr
1               5

<210> SEQ ID NO 13
<211> LENGTH: 12
<212> TYPE: PRT
<213> ORGANISM: Artificial Sequence
<220> FEATURE:
<223> OTHER INFORMATION: rs-pharmacophore

<400> SEQUENCE: 13

His Ile Lys Leu Met Asn Pro Gln Arg Val Trp Tyr
1               5                   10

<210> SEQ ID NO 14
<211> LENGTH: 6
<212> TYPE: PRT
<213> ORGANISM: Artificial Sequence
<220> FEATURE:
<223> OTHER INFORMATION: synthetic peptide

<400> SEQUENCE: 14

Gln Glu Asp Thr Asn Phe
1               5

<210> SEQ ID NO 15
<211> LENGTH: 9
<212> TYPE: PRT
<213> ORGANISM: Artificial Sequence
<220> FEATURE:
<223> OTHER INFORMATION: rs-pharmacophore

<400> SEQUENCE: 15

His Asn Pro Gln Arg Ser Thr Trp Tyr
1               5

<210> SEQ ID NO 16
<211> LENGTH: 9
<212> TYPE: PRT
<213> ORGANISM: Artificial Sequence
<220> FEATURE:
<223> OTHER INFORMATION: rs-pharmacophore

<400> SEQUENCE: 16

His Lys Asn Pro Gln Arg Thr Trp Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: rs-pharmacophore

<400> SEQUENCE: 17

```
Lys Asn Gln Arg Thr Trp Tyr
1               5
```

<210> SEQ ID NO 18
<211> LENGTH: 6
<212> TYPE: PRT
<213> ORGANISM: Artificial Sequence
<220> FEATURE:
<223> OTHER INFORMATION: rs-pharmacophore

<400> SEQUENCE: 18

```
Asp Glu Pro Gln Ser Tyr
1               5
```

<210> SEQ ID NO 19
<211> LENGTH: 6
<212> TYPE: PRT
<213> ORGANISM: Artificial Sequence
<220> FEATURE:
<223> OTHER INFORMATION: rs-pharmacophore

<400> SEQUENCE: 19

```
Phe Ile Met Val Trp Tyr
1               5
```

<210> SEQ ID NO 20
<211> LENGTH: 16
<212> TYPE: PRT
<213> ORGANISM: Artificial Sequence
<220> FEATURE:
<223> OTHER INFORMATION: rs-pharmacophore

<400> SEQUENCE: 20

```
Asp Phe His Ile Lys Leu Met Asn Pro Gln Arg Ser Thr Val Trp Tyr
1               5                   10                  15
```

<210> SEQ ID NO 21
<211> LENGTH: 8
<212> TYPE: PRT
<213> ORGANISM: Artificial Sequence
<220> FEATURE:
<223> OTHER INFORMATION: rs-pharmacophore

<400> SEQUENCE: 21

```
Lys Asn Gln Arg Ser Thr Trp Tyr
1               5
```

<210> SEQ ID NO 22
<211> LENGTH: 8
<212> TYPE: PRT
<213> ORGANISM: Artificial Sequence
<220> FEATURE:
<223> OTHER INFORMATION: rs-pharmacophore

<400> SEQUENCE: 22

```
His Lys Asn Gln Arg Thr Trp Tyr
1               5
```

<210> SEQ ID NO 23
<211> LENGTH: 4
<212> TYPE: PRT
<213> ORGANISM: Artificial Sequence
<220> FEATURE:
<223> OTHER INFORMATION: synthetic peptide

<400> SEQUENCE: 23

```
Lys Arg Asn Gln
```

```
<210> SEQ ID NO 24
<211> LENGTH: 8
<212> TYPE: PRT
<213> ORGANISM: Artificial Sequence
<220> FEATURE:
<223> OTHER INFORMATION: rs-pharmacophore

<400> SEQUENCE: 24

His Lys Asn Gln Arg Ser Trp Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: rs-pharmacophore

<400> SEQUENCE: 25

Asp Glu Phe His Ile Lys Leu Met
1               5

<210> SEQ ID NO 26
<211> LENGTH: 8
<212> TYPE: PRT
<213> ORGANISM: Artificial Sequence
<220> FEATURE:
<223> OTHER INFORMATION: rs-pharmacophore

<400> SEQUENCE: 26

Asn Pro Gln Arg Thr Val Trp Tyr
1               5

<210> SEQ ID NO 27
<211> LENGTH: 6
<212> TYPE: PRT
<213> ORGANISM: Artificial Sequence
<220> FEATURE:
<223> OTHER INFORMATION: synthetic peptide

<400> SEQUENCE: 27

Asp Gln Glu Asn Ser Tyr
1               5

<210> SEQ ID NO 28
<211> LENGTH: 8
<212> TYPE: PRT
<213> ORGANISM: Artificial Sequence
<220> FEATURE:
<223> OTHER INFORMATION: rs-pharmacophore

<400> SEQUENCE: 28

Asp Glu Phe His Leu Met Asn Pro
1               5

<210> SEQ ID NO 29
<211> LENGTH: 7
<212> TYPE: PRT
<213> ORGANISM: Artificial Sequence
<220> FEATURE:
<223> OTHER INFORMATION: rs-pharmacophore

<400> SEQUENCE: 29

Gln Arg Ser Thr Val Trp Tyr
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: rs-pharmacophore

<400> SEQUENCE: 30

Asp Glu Asn Pro Gln Ser Thr Tyr
1               5

<210> SEQ ID NO 31
<211> LENGTH: 6
<212> TYPE: PRT
<213> ORGANISM: Artificial Sequence
<220> FEATURE:
<223> OTHER INFORMATION: rs-pharmacophore

<400> SEQUENCE: 31

Asp Glu Asn Gln Ser Thr
1               5

<210> SEQ ID NO 32
<211> LENGTH: 7
<212> TYPE: PRT
<213> ORGANISM: Artificial Sequence
<220> FEATURE:
<223> OTHER INFORMATION: rs-pharmacophore

<400> SEQUENCE: 32

His Asn Pro Gln Ser Thr Trp
1               5

<210> SEQ ID NO 33
<211> LENGTH: 14
<212> TYPE: PRT
<213> ORGANISM: Artificial Sequence
<220> FEATURE:
<223> OTHER INFORMATION: rs-pharmacophore

<400> SEQUENCE: 33

His Ile Lys Leu Met Asn Pro Gln Arg Ser Thr Val Trp Tyr
1               5                   10
```

MUTANT VARIANTS OF PD-1 RECEPTOR WITH SELECTIVE BINDING TO PD-L1 AND USES THEREOF

CROSS-REFERENCE TO RELATED APPLICATION

This application claims the benefit of U.S. Provisional Patent Application No. 62/736,477, filed on Sep. 26, 2018, the content of which is herein incorporated by reference in its entirety.

STATEMENT OF GOVERNMENT SUPPORT

This invention was made with government support under grant numbers GM118709 and HG008325 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Lymphocyte activation requires two signals mediated by protein-protein interactions: the T-cell receptor (TCR) interaction with antigenic peptide/MHC complex that provides the specificity of the immune response and an antigen-independent co-modulatory signal that modulates T-cell clonal expansion and acquisition of effector function (1). Engagement of co-stimulatory receptors such as CD28 and ICOS with their cognate B7 family ligands expressed on antigen presenting cells results in T cell activation and proliferation. In contrast, engagement of cytotoxic T lymphocyte associate antigen (CTLA-4), programmed cell death protein (PD-1), and B- and T-lymphocyte attenuator (BTLA) with their corresponding ligands negatively regulate T cell activation (2).

PD-1 is a type I transmembrane protein, composed of an extracellular immunoglobulin variable (IgV) domain, a transmembrane domain, and an intracellular domain with tyrosine-based signaling motifs (3). The PD-1 ligands, PD-L1 (4) and PD-L2 (5), are also type I transmembrane proteins, and possess ectodomains composed of tandem IgV and immunoglobulin constant (IgC) domains, a single pass helical transmembrane region and a cytoplasmic domain (6, 7). T cells, natural killer T cells, B cells, and some myeloid cells express PD-1 receptor (6). PD-L1 is constitutively expressed on mouse immune cells such as T cells, B cells and dendritic cells (DCs) (8). Nonhematopoietic cells can also express PD-1, with expression levels depending on a variety of other stimuli (6). Expression of PD-L2 is limited to DCs, macrophages, and bone marrow-derived mast cells (5).

Engagement of PD-1 with either of its two known ligands, PD-L1 (B7-H1) or PD-L2 (B7-DC) from the B7 family (9), provides inhibitory signals that control autoimmune responses by maintaining immune tolerance to self-antigens (10). PD-1 signaling also makes important contributions to responses against microbial pathogens. Persistent PD-1 expression can cause T cell exhaustion that reduces anti-viral and anti-tumor immune responses, and leads to unfavorable disease progression by inhibiting T-cell proliferation and cytotoxicity, as well as cytokine production (11). Blockade of the PD-1 pathway can reverse T-cell exhaustion and enhance anti-tumor responses (12). Malignant cells utilize a range of mechanisms to evade host immune surveillance, including the overexpression of PD-L1 on their surface, which can result in a highly immune-suppressive milieu in the tumor microenvironment (13, 14). Therapeutic agents, especially monoclonal antibodies (mAbs), have been developed to block the PD-1 signaling pathways (15) and have shown activity against several cancers, with FDA approval for multiple indications (16, 17). Among these, nivolumab and pembrolizumab have shown clinical efficacy for the treatment of metastatic melanoma, non-small cell lung cancer and other malignancies (18). Similarly, re-invigorating T cells through PD-1 blockade can elicit beneficial immune responses in chronic viral infections (19-21). In order to further increase potency, engineered T cells have been combined with other therapeutics targeting the PD-1 signaling pathway (22, 23). However, mAbs have inherent limitations such as antigenicity, poor tissue penetrance due to their large size (~150 kDa) and detrimental Fc-effector functions that deplete immune cells (24). As a complementary approach to mAbs, PD-1 ectodomains and their engineered variants could be used to interrupt the PD-1 pathway by directly binding to the PD-ligands. Directed evolution via yeast-surface display has been used to engineer a PD-1 variant that specifically antagonizes PD-L1. The resulting PD-1 construct had 10 residues mutated compared to wild type PD-1, resulting in a 15-40 thousand fold increase affinity to PD-L1, while not binding to PD-L2 (25). While possessing remarkable affinity and selectivity, the large number of altered residues could result in undesirable antigenic properties, making variants with the smallest number of mutations desirable. In a recent study, a cross-reactive single mutant (A132L) in PD-1 was reported to enhance binding activity to PD-L1 and PD-L2 by 45- and 30-fold, respectively, compared with wild type PD-1 (26).

Computational protein design methods generate and assess large numbers of sequence variants at predetermined binding surfaces. These approaches dramatically reduce the number of designs for subsequent experimental evaluation (27, 28). Computational design algorithms have been used to design new folds (29), enzymatic functions (30), and novel binding functions (31). Computational approaches for optimizing selectivity often require both positive design considerations to stabilize the desired interactions and negative design considerations to distinguish among a number of sequence and structurally similar competitor molecules (32, 33).

In the context of PD-1 pathway modulation, our goal is to computationally redesign the ligand recognition surface of PD-1 to antagonize the PD-1:PD-L2 interaction, while maintaining or enhancing the affinity of the PD-1:PD-L1 interaction. We utilized our recently developed ProtLID (Protein Ligand Interface Design) method to predict residue-based pharmacophore (rs-pharmacophore) signatures over the binding surface for PD-L1 and PD-L2 (34). We then compared these rs-pharmacophores with the known binding interfaces of PD-1 predicted positions and residue types to alter specificities. In subsequent cell-based assays, we validated a number of these designs. Half of all predicted single mutant PD-1 designs exhibited statistically significantly reduced interaction with PD-L2, nine of which maintained close to wild type interaction with PD-L1, and among these, three designs showed no detectable affinity to PD-L2. These new constructs are both reagents and promising drug leads for modulation of the PD-1 pathway.

The present invention addresses the need for PD-1 receptor mutants having selectivity for PD-LI compared to PD-L2 that can be used for imaging and treatments.

SUMMARY OF THE INVENTION

The present invention provides human Programmed Cell Death-1 (PD-1) receptor mutants comprising mutation N66Q, Y68N, Y68K, Y68R, Y68Q, S73R, Q75N, T76D, T76E, D77E, K78R, G124V, L128V, K131H, I134N or I134F, wherein the mutation is relative to the amino acid sequence set forth in SEQ ID NO:1 or in NCBI Reference Sequence NP 005009.2, and wherein the mutant has selectivity for PD-LI compared to PD-L2. Preferably, the mutant corresponds to a mutated version of at least the first 149 amino acids of SEQ ID NO:1.

Also provided are methods of obtaining the mutants and uses of the mutants for imaging and treating tumors and infections.

BRIEF DESCRIPTION OF THE DRAWINGS

FIG. 1A-1C. Sequence alignments derived from DALI (38) structural superpositions. Pairwise alignment between orthologs of PD1: (A) human and mouse PD-1 (hPD-1 (SEQ ID NO:2) and mPD-1 (SEQ ID NO:3)), and (B) human and mouse PD-L2 (hPD-L2 (SEQ ID NO:4) and mPD-L2 (SEQ ID NO:5)). (C) Alignment between Ig-like variable-type domain of hPD-L1 (SEQ ID NO:6) and hPD-L2 (SEQ ID NO:7). '*' indicates conserved interface residues; '–' refers non-conserved interface residues; '+' indicates a conserved residue that is not part of the interface in mPD-1. All structures and homology models were energetically relaxed in a 25 ns long molecular dynamics simulation prior to superposition. The amino acid numbering refers to the first sequence within each pairwise alignment.

FIG. 2A-2C. Experimental testing of selectivity of PD-1 mutants. (A) Flow cytometric analysis of hPD-1 mutants binding to PD-L1 and PD-L2. A set of 32 human PD-1 mutants were cloned and transiently expressed in suspension HEK 293 cells. Cells were challenged with 0.25 μg recombinant hPD-L1 or hPD-L2 hIgG1 Fc-fusion protein and detected with goat anti-human Alexa 488 secondary antibody. Flow cytometric analysis was used to determine the percent of PD-1 positive cells bound to PD-L1 or PD-L2. The data represents the average of three independent experiments with error bars showing the standard deviation. (B, C) Titration of hPD-1 mutants shows selective binding to PD-L1. (B) HEK 293 suspension cells transiently expressing WT or mutant PD-1 were challenged with increasing concentrations of hPD-L1 hIgG1 (0.1-200 nM) and FACS analysis was used to determine the percent of PD-1 expressing cells (mCherry) bound to PD-L1 (Alexa 488). For each experiment, the titration data was normalized to wild-type PD-1 binding to the highest concentration of PD-L1 (200 nM). Normalized data was plotted in Graphpad Prism software and EC50s were estimated using the three parameter dose response non-linear regression analysis $Y=B_{min}+(B_{max}-B_{min})/(1+10^{\wedge}((\text{Log EC50-X})))$. Data shown represents four independent experiments with standard deviation. (B) The same analysis as shown in (B) except titrating hPD-L2 hIgG1 protein. EC50s could not be estimated for Y68R and Y68K (N/A) as no detectable binding was observed within the range of concentrations analyzed.

FIG. 3A-3C. Impact of single point mutations. (A) BeAtMuSiC (1), (B) FOLDX (2), and (C) MutaBind (3) results for assessing the impact of single point mutations. The first column in each pair represents PD-1(PD-1/PD-L1); the second column in each pair represents PD-1(PD-1/PD-L2).

DETAILED DESCRIPTION OF THE INVENTION

The present invention provides a human Programmed Cell Death-1 (PD-1) receptor mutant comprising at least the first 149 consecutive amino acids of SEQ ID NO:1 with mutation N66Q, Y68N, Y68K, Y68R, Y68Q, S73R, Q75N, T76D, T76E, D77E, K78R, G124V, L128V, K131H, I134N or I134F, wherein the mutant has selectivity for PD-LI compared to PD-L2.

The first 149 amino acids of SEQ ID NO:1 covers the soluble first ectodomain of PD1 mutants, i.e. what is shown in the alignment FIG. 1, the first 149 residiues from the N-terminal or the first IG-V domain (IGV-PD1).

In an embodiment, the mutant comprises or consists of SEQ ID NO:1 with mutation N66Q, Y68N, Y68K, Y68R, Y68Q, S73R, Q75N, T76D, T76E, D77E, K78R, G124V, L128V, K131H, I134N or I134F, wherein the mutant has selectivity for PD-LI compared to PD-L2.

In one embodiment, the mutation is selected from the group consisting of N66Q, Y68N, Y68K, Y68R, Y68Q, S73R, Q75N, T76D, T76E, D77E, K78R, G124V, L128V, K131H, I134N and I134F, wherein the mutant has selectivity for PD-LI compared to PD-L2.

In one embodiment, the mutant is Y68R or Y68K, where the mutant has undetectable PD-L2 binding. In one embodiment, the mutant is Y68N, T76D or T76E, where the mutant has a 4-12 fold selectivity for PD-L1 compared to PD-L2.

In one embodiment, the mutant achieved selectivity by diminishing PD-1 binding to PD-L2.

In a preferred embodiment, the mutation is a single amino acid mutation.

In an embodiment, the un-mutated human full-length PD-1 has the following sequence:

(SEQ ID NO: 1)

```
MQIPQAPWPVVWAVLQLGWRPGWFLDSPDRPWNPPTFSPALLVVTEGDN

ATFTCSFSNTSESFVLNWYRMSPSNQTDKLAAFPEDRSQPGQDCRFRVT

QLPNGRDFHMSVVRARRNDSGTYLCGAISLAPKAQIKESLRAELRVTER

RAEVPTAHPSPSPRPAGQFQTLVVGVVGGLLGSLVLLVWVLAVICSRAA

RGTIGARRTGQPLKEDPSAVPVFSVDYGELDFQWREKTPEPPVPCVPEQ

TEYATIVFPSGMGTSSPARRGSADGPRSAQPLRPEDGHCSWPL.
```

In an embodiment, the mutant is a mutant relative to NCBI Reference Sequence NP_005009.2.

In an embodiment, the mutant comprises the sequence set forth in SEQ ID NO:1 or in NCBI Reference Sequence NP_005009.2, with one of the mutations specified herein. In an embodiment, the mutant consists of the sequence set forth in SEQ ID NO:1 or in NCBI Reference Sequence NP_005009.2, with one of the mutations specified herein.

As described herein, the mutant PD-1 mutant is a not a naturally occurring PD-1 mutant.

The invention further provides a fusion polypeptide comprising any of the PD-1 receptor mutants disclosed herein fused to an immunoglobulin domain polypeptide. Preferably, the mutant is fused to the immunoglobulin domain polypeptide by a peptide bond between a terminal amino acid of the mutant and a terminal amino acid of the immunoglobulin domain polypeptide. Preferably, the immunoglobulin domain polypeptide comprises an immunoglobulin IgG1 Fc domain. Preferably, the immunoglobulin IgG1 Fc domain is human.

Also provided is a composition comprising any of the PD-1 receptor mutants disclosed herein or any of the fusion polypeptides disclosed herein, and a pharmaceutically acceptable carrier. As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000).

The invention also provides a method of stimulating T cell activation, treating a tumor, or treating an infection in a subject comprising administering to the subject any of the PD-1 receptor mutants disclosed herein or any of the fusion polypeptides disclosed herein, or any of the compositions disclosed herein in an amount effective to stimulate T cell activation, treat a tumor, or treat an infection, respectively, in a subject.

As used herein, to "treat" a tumor means to reduce the size of the tumor or to stabilize the tumor so that it does not increase in size. In an embodiment, the tumor is a tumor of the breast, lung, colon, ovarian, melanoma, bladder, liver, salivary, stomach, gliomas, thyroid, thymus, epithelial, head, or neck. In an embodiment, the tumor is a hematological malignancy. In an embodiment, the tumor is a lymphoma. In an embodiment, the tumor is a myeloma. In an embodiment, the tumor is a multiple myeloma.

As used herein, to "treat" an infection means to reduce a sign or symptom of the infection or to eliminate the infection from the subject. In an embodiment, the infection is a viral Infection. In a further embodiment, the virus is a HIV, HCV, HBV or HTLV. In an embodiment, the infection is a bacterial, fungal, protozoal or parasitic infection. In embodiments, the infection is caused by *Helicobacter pylori*, the fungus *Histoplasma capsulatum*, the parasite *Taenia crassiceps* or *Schistosoma mansoni*, or the protozoa *Leishmania mexicana*.

The invention also provides any of the PD-1 mutants disclosed herein further comprising a radiolabel. Also provided is a method of imaging a PD-L1 positive tumor in a subject comprising administering the radiolabeled PD-1 mutant to the subject, where the mutant binds to the tumor, and imaging the radiolabeled mutant bound to the tumor. Radioisotopes that can be used for radioimmunoimaging include, but are not limited to, 99m-Technetium, 111-Indium, 67-Gallium, 123-Iodine, 124-Iodine, 131-Iodine, 11-Carbon and 18-Fluorine. Imaging modalities that can be used include positron-emission tomography (PET), single-photon emission computed tomography (SPECT), and scintigraphy (gamma scan).

In a preferred embodiment of the methods, the subject is a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

In the context of PD-1 pathway modulation, the present goal was to computationally redesign the ligand recognition surface of PD-1 to antagonize the PD-1:PD-L2 interaction, while maintaining or enhancing the affinity of the PD-1:PD-L1 interaction. We utilized a recently developed ProtLID (Protein Ligand Interface Design) method to predict residue-based pharmacophore (rs-pharmacophore) signatures over the binding surface for PD-L1 and PD-L2 (34). We then compared these rs-pharmacophores with the known binding interfaces of PD-1 predicted positions and residue types to alter specificities. In subsequent cell-based assays, we validated a number of these designs. Half of all predicted single mutant PD-1 designs exhibited statistically significantly reduced interaction with PD-L2, nine of which maintained close to wild type interaction with PD-L1, and among these, three designs showed no detectable affinity to PD-L2. These new constructs are both reagents and promising drug leads for modulation of the PD-1 pathway.

Material and Methods

PD-1, PD-L1, and PD-L2 proteins and their complexes. The crystallographic structures of the human ectodomains of PD-1 and PD-L1 complex (4ZQK) were recently published (35). The hPD-1 and hPD-L2 complex is not available, but the structure of the orthologous mouse mPD-1:mPDL2 (PDB ID: 3BP5) complex has been determined (36). Since hPD-1 and mPD-1 proteins share 64% sequence identity, a computational homology model for the hPD-1:hPD-L2 complex was generated for this study (48-50), using the mPD-1:mPD-L2 complex and hPD1 (5GGS.Y) as the templates.

ProtLID, residue-specific pharmacophore approach for interface design. We recently developed a residue-based pharmacophore (rs-pharmacophore) approach for interface design (ProtLID, Protein Ligand Interface Design) that was used to identify cognate ligand binding partners for given target proteins (34). In this current application, we used ProtLID to generate rs-pharmacophores for the interfaces of ligand proteins (PD-L1 and PD-L2) in order to identify the ideal matching three-dimensional residue pattern signatures (rs-pharmacophore). These rs-pharmacophores were compared with each other and with the wild type receptor interface to identify differences that could be utilized to design ligand-specific single mutant variants of hPD-1. The rs-pharmacophore generation consists the steps indicated below.

Identify interface residues. Interface residues for hPD-L1 (4ZQK.A) and mPD-L2 (3BP5.B) were identified with the CSU program (39): residues interacting between the receptor and ligand were identified if these satisfied CSU classification for legitimate interactions and the nearest atomic distance fell within 4.0 Å (39). Interface residues were required to have at least 1 $Å^2$ accessible surface area.

Mesh generation over interface residues. A hypothetical mesh was constructed over the interface of the ligands, using a 1 Å distance and probe radius over the solvent accessible region of the interface residues of hPD-L1 and mPD-L2 (51). These mesh points served as starting points for subsequent MD simulations.

Single-residue probe simulation using molecular dynamics. Extensive molecular dynamics (MD) simulations were performed for hPD-L1 and mPD-L2 from each mesh point constructed over their interfaces using AMBER (52) with seven replicas, each with different starting orientations using the 20 amino acid residues as probes. The system was minimized from 5.0 kcal/mol to 0 with 5000 steps using harmonic restraints on heavy atoms and simulated to 30 ps using the Generalized Born implicit solvation model with no periodic boundary condition at 300 K, using Andersen thermal coupling. The system contains either hPD-L1 or mPD-L2, with single-residue probes (uncapped N-terminal N—H and C-terminal C=O). Each probe residue is uniquely defined by one or more side-chain atoms that represent the most characteristic chemical functional group—these were defined as functional atoms (FA). There are 26 FAs to define 18 amino acids (non-specific mainchain interactions were not considered, and consequently neither Gly nor Ala). For example, the amino acid Trp is represented by aromatic ring center (RC_W) and hydrogen-bond donor (NE1_W) (34).

Functional atom preference over the mesh point. The propensity of a FA in the proximity of the mesh point determines residue preferences in various spatial locations. Actual preferences are estimated using the actual to expected (A/E) ratio. The A/E ratio compares the actual FA propensity to the expected FA propensities observed from the similar interaction of all snapshots nearest to the mesh point, and as such implicitly accounts for geometrical artifacts on the molecular surface. In addition, only legitimate molecular interactions were considered such as hydrogen bond acceptor-donor or hydrophobic contacts according to CSU definitions (34).

Match the predicted rs-pharmacophores with the interface residues of PD-1. The calculated rs-pharmacophore for hPD-L1 (4ZQK.A) is then matched with the known residues from the interaction surface of hPD-1 (4ZQK.B) and similarly, the pharmacophores calculated for mPD-L2 (3BP5.B) were matched to mPD-1 (3BP5.A) using CSU (39). When multiple residues are in close proximity, the union of their suggested variants was considered. The rs-pharmacophores generated using hPD-L1 and mPD-L2 (equivalent residues with hPD-L2) were compared with one another and with the observed interface of hPD-1 to select hPD-1 mutants with selectivity for hPD-L1.

Site-directed mutagenesis of human PD-1 variants. The coding sequence for the full-length ectodomain of human PD-1 (Leu 25-Thr 168) was cloned by ligation-independent cloning into a vector that adds the leader sequence from erythropoietin (EPO) and the transmembrane domain from mouse PD-L1 followed by mCherry (hPD-1 Type I mCherry). Site-specific mutagenesis was performed as described previously using high fidelity KOD polymerase (53). After two rounds of primer design, 32 of the 34 predicted mutations were successfully cloned and sequence validated (94% success rate). These mutants were tested for expression by transient transfection of 1 mL suspension HEK 293 cells. Prior to utilization in downstream binding experiments, all of the hPD-1 mutants were shown to express at levels comparable to the parental hPD-1 construct as analyzed by FACS and showed correct membrane localization as observed by fluorescence microscopy.

Analysis of PD-1 variants binding to PD-L1 and PD-L2 by high-throughput flow cytometry. Wild-type and mutant hPD-1 constructs were transiently transfected into 1 mL suspension of HEK 293 cells at a density of $1\times10^6$ cells/mL in 24-well plates using 0.5 μg plasmid DNA and 2 μg linear PEI. Two days post transfection, cells were counted and diluted to $1\times10^6$ cells/mL with 1×PBS with 2% BSA. In 96-well V-bottom plates, 100,000 cells were challenged with 0.1 μg of hPD-L1 or hPD-L2 Fc-fusion protein (R&D Systems) for 1 hour at room temperature while shaking in a 96-well plate shaker at 900 rpm. Cells were subsequently pelleted by centrifugation at 500×g and washed with 1×PBS with 2% BSA two times. Goat anti-human Alexa 488 secondary antibody (0.25 μg) was added to the cells and they were incubaed at 4° C. for 45 min. After washing three times, antibody binding was assessed by FACS analysis on a BD Accuri cytometer connected to an Intellicyt Hypercyte auto sampler. Flow data were gated for mCherry positive events (hPD-1 expression) and then sub-gated for hPD-L1/L2 binding (Alexa 488 channel). The experiment was performed in triplicate and the data from each experiment were normalized to wild type PD-1 binding.

For titration experiments, WT and selected PD-1 mutants were transiently transfected as described above. Two days post transfection cells were diluted to $1\times10^6$ cells/mL with 1×PBS with 2% BSA and 100,000 cells were challenged with increasing concentrations of hPD-L1 hIgG1 or hPD-L2 hIgG1 (R&D Systems) from 0.1-200 nM final concentrations. After binding for 1 hour at room temperature, the cells were washed once with 1×PBS with 2% BSA and goat anti-human Alexa 488 secondary antibody (0.25 μg) was added. After incubation with secondary antibody, the cells were washed twice with 1×PBS with 2% BSA and analyzed by FACS as described above. The percent of PD-1 expressing cells bound to either PD-L1 or PD-L2 was determined and the data normalized to the highest ligand concentration for wild-type PD-1 binding. The EC50s were estimated by plotting the normalized titration data in Graphpad Prism software and fitting the data using the equation for a three-parameter dose response non-linear regression analysis $Y=B_{min}+(B_{max}-B_{min})/(1+10^{(LogEC50-X)})$.

Results

Residue-specific pharmacophore generation. Understanding the intermolecular interactions between PD-1 and its two cognate ligands (PD-L1 and PD-L2) can help selectively block the PD-1 signaling pathway for mechanistic analysis and potentially provide therapeutic leads. We focused on redesigning the human PD-1 (hPD-1) interface to selectively bind to hPD-L1 (positive design), but not to hPD-L2 (negative design), to obtain a selective reagent.

hPD-1 and hPD-L1 contribute 15 and 12 residues, respectively, to the recognition interface (4ZQK) (35) (FIG. 1, Table 1). As there is no existing structure of the human PD-1:PD-L2 complex, the murine mPD-1:mPD-L2 complex (3BP5) (36) was used as a proxy. Out of the 14 interface residues shared between hPD-1 and mPD-1, 11 residues (N66, S73, Q75, T76, K78, G124, I126, K131, A132, I136, and E136) are identical. In the case of PD-L2, 10 out of 14 interface residues (F21, E28, Q60, S67, I105, W110, D111, Y112, K113, and Y114) are identical between hPD-L2 and mPD-L2 orthologs (FIG. 1, Table 1). A computational homology model (37) was built for hPD-1:hPD-L2 using hPD1 and mPD-1:mPD-L2 as a template; these orthologs share 64% and 70% overall sequence identity for the entire length of the proteins, respectively. Superposition of the hPD-1 and mPD-1 structures with DALI (38) resulted in $C_\alpha$-RMSD=1.8 Å over 107 out of 113 residues. Interface residues were identified by the CSU program (39): by this definition, K98 of mPD-1 is not part of the interface of mPD-1:mPD-L2 complex, although K98 of mPD-1 aligns with K131 of hPD-1.

In order to design a PD-L1-specific interface on hPD-1, we used our recently developed computational algorithm, ProtLID, to generate residue-based pharmacophores (rs-pharmacophores) for the hPD-L1 and mPD-L2 interfaces. Rs-pharmacophores are descriptions of idealized complementary interacting surface patches to these ligands, which are obtained through the analysis of single amino acid binding preferences after an extensive molecular dynamics simulation. When the calculated rs-pharmacophore for hPD-L1 is compared with the actual binding residues of hPD-1, 10 out of 15 wild-type residues (67%) were correctly recapitulated (Table 1). Likewise, 11 out of 19 (58%) wild-type binding residues of mPD-1 were recapitulated, of which six (N66, Q75, T76, K78, I126, and E136) were identical to hPD-1 interface residues. Four residues are conserved between the interfaces of hPD-L1 and hPD-L2 (the PD-L2 interface residues were obtained through the comparative model built using the mPD-1:mPD-L2 experimental structure) (Table 1).

Figures 2B, 2C:
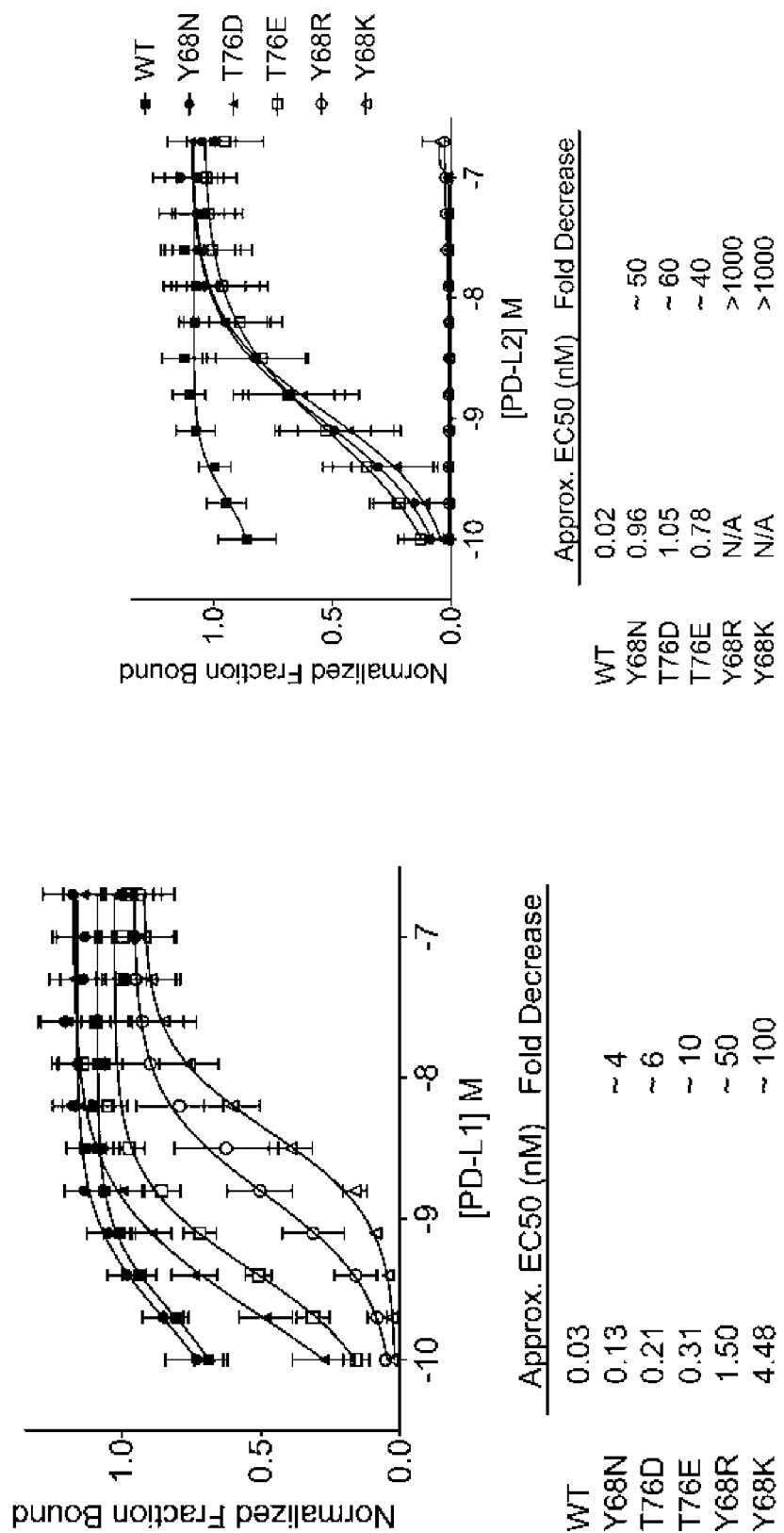

Selecting single mutant designs. Differences between the rs-pharmacophores generated for each ligand and the observed interface of wild type hPD-1 suggested residue types and positions to modify for enhanced PD-L1 selectivity (Table 1). One set of design targets consisted of positions where the two ligands (PD-L1 and PD-L2) have different residues interacting with the receptor (PD-1), and there were also differences between the rs-pharmacophores designed for these ligand residues. These differences can be utilized to suggest mutations that selectively prefer only one ligand. For instance, in the case of K133 in hPD-1, the interacting residue in hPD-L1 is Q66, while in both hPD-L2 and mPD-L2 it is S67. The differences between the calculated rs-pharmacophores suggest that hPD-L1 uniquely preferred H and P as interacting partners. After visual inspection of the local structural environment, the K131H variant was selected for testing. Other selections involved cases where both ligands had the same residue type interacting with the receptor, but the calculated rs-pharmacophores, influenced by other residues in the environment, suggested differences in preferences between the two ligands. An example is F19 in hPD-L1 (and the equivalent F21 in mPD-L2), interacting with K78 in hPD-1. The rs-pharmacophore for hPD-L1 had two unique residue preferences, R and T, which are not preferred by PD-L2. After visual inspection, we tested K78R, which in a subsequent cell assay showed selective binding to hPD-L1, relative to hPD-L2 (FIG. 2.).

Other design elements required more elaboration due to the complex network of interactions between interface residues, which are not readily deconvolved into simple pairwise contacts. These positions often exhibit "promiscuity", as they can accommodate a wider range of amino acid substitutions. Once these positions are identified from rs-pharmacophore preferences, they provide a more flexible target environment for exploration. For instance, one of the conserved interface residues is Y123 of hPD-L1, the equivalent of which is Y112 in mPD-L2 (and is also identical in hPD-L2). The calculated rs-pharmacophores for the two ligands suggested similar complementary interacting patches, to accommodate the two "Functional Atoms" of Tyr (aromatic ring center and hydroxyl group). The rs-pharmacophore contains residues that are hydrogen-bond donors or acceptors (DEPNQRHT) (SEQ ID NO:8), hydrophobic (LM), and aromatic (FYW) (Table 1). The wide spectrum of tolerated residues in the rs-pharmacophore is explained by the interacting region on the hPD-1 receptor side, where six residues with diverse properties are found in spatial proximity to Y123 of hPD-L1, including hydrogen-bond acceptors or donors (E136, G124 and T76), hydrophobic (I126, I134), and aromatic (Y68) residues. The corresponding residue in mPD-L2, Y112 interacts with hydrogen-bond acceptors or donors (N35, E103 and T43) and a hydrophobic residue (I101) in the wild type interface of mPD-1. Interestingly, E136 (E103), T76 (T43), and I134 (I101) are conserved residues between mPD-1 and hPD-1. Once the rs-pharmacophore was rationalized in this local context, a total of 10 mutations were explored in three positions of hPD1. Two of these variants, T76D and T76E, achieved high selectivity for PD-L1 (Table 1).

Another promising location that was revealed by the rs-pharmacophore analysis was position Y68 in hPD-1 of which the equivalent is N35 in mPD-1; however, despite being different residue types, both interact with an Tyr in hPD-L1 (Y123) and mPD-L2, (Y112). Y68 is part of a cluster of interacting residues in hPD-1, whose members include K78, E136, G124, I126, I134, and T76, making the resulting rs-pharmacophores relatively accommodating and suggesting a highly tolerant position ripe for exploration. We explored six mutants for Y68, four of which induced selectivity for PD-L1 (FIG. 2).

Experimental validation. After excluding all the previously studied mutations (25, 26), we prioritized 34 mutants covering 14 residues in hPD-1 for experimental validation. Site directed mutagenesis was performed, resulting in 32 single point mutations, which were all sequence validated and expressed as GFP fusions presented on the surface of suspension adapted HEK-293 cells. Analysis of the hPD-1 mutants binding to hPD-L1 and hPD-L2 was performed by high-throughput flow cytometry. The percent of hPD-1-expressing cells bound to either hPD-L1 or hPD-L2 was determined and the data normalized to the highest ligand concentration for wild-type hPD-1 binding. Out of the 32 hPD-1 mutants, 16 (N66Q, Y68N, Y68K, Y68R, Y68Q, S73R, Q75N, T76D, T76E, D77E, K78R, G124V, L128V, K131H, I134N, I134F) showed statistically significant ($p<0.05$, two-tailed t-test) increases in selectivity towards PD-L1 (Table 2). Of these, six maintained close to wild type binding interaction to PD-L1. We selected five of these designs for titration experiments, where HEK-293 cells expressing WT or mutant hPD-1 were challenged with hPD-L1 or hPD-L2 expressing cells (FIG. 2). Two mutants, Y68R and Y68K, showed undetectable PD-L2 binding, while EC50 values for PD-L1 were 1.50 and 4.48 nM, respectively. The other three mutants (Y68N, T76D and T76E) showed a 4-12 fold selectivity for PD-L1. All the successful mutants achieved selectivity by diminishing PD-1 binding to PD-L2, but none of the selectivity was achieved by increasing PD-1 binding to PD-L1 in a statistically significant manner.

Structural insights. We generated comparative protein structure models to gain further insight about mutations that achieved high selectivity between the two ligands. The models of the complexes were subject to 25 ns molecular dynamics simulations using GROMACS (40) to accommodate the rearrangement of local contacts. Interestingly, the Y68 mutant interacts with a highly conserved cluster of residues on hPD-L1 and hPD-L2, which includes D122 (D111 for hPD-L2), Y123 (Y112), K124 (K113). However, the modeling suggests that residue A121 in hPD-L1 (W110 in hPD-L2) is the most relevant for recognition of Y68 of PD-1. When mutated to long, polar side chains (i.e., Y68R and Y68K), a possible steric conflict emerged with W110 of hPD-L2, despite the otherwise favorable complementary charge interactions. When a shorter side chain is introduced, Y68N, selectivity is still achieved, but to a lesser extent.

When exploring the other most selective site for mutation, hPD-1 T76D or T76E, it appears that a more favorable charged or hydrogen bond interaction is established with R125 and K124 of PD-L1, while the Y114 side chain of hPD-L2 is not suitable to support this mutant.

Figure 3A:
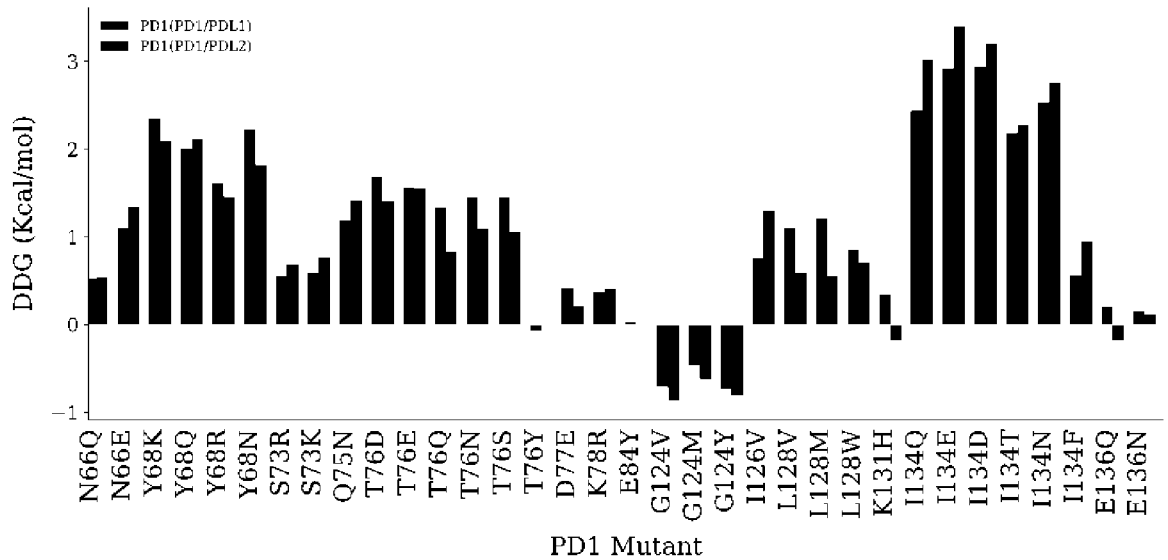
Figure 3B:
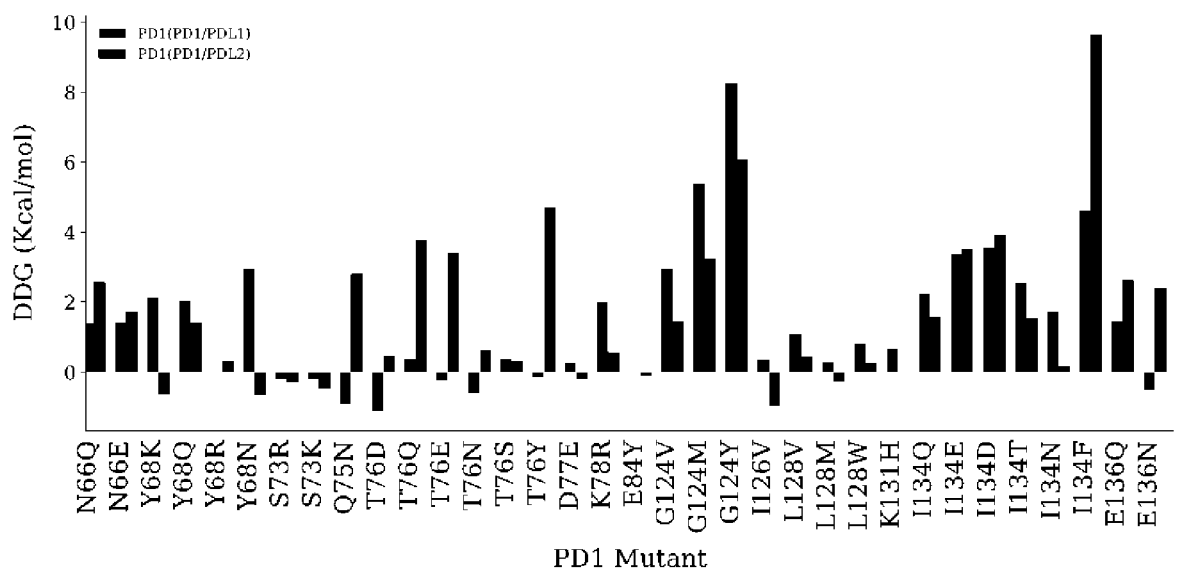
Figure 3C:
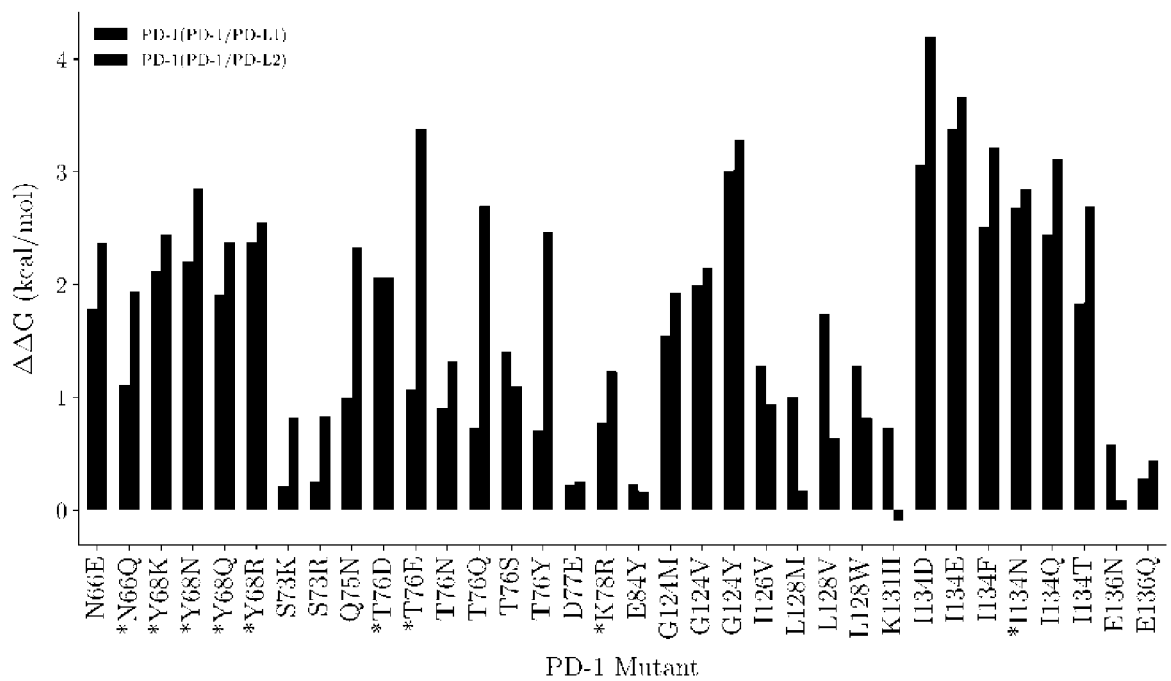

Correlation with predicted free energy changes. Once experimental data were obtained we also attempted to retrospectively correlate the results with methods that predict the energetic effect of point mutations. We ran three different programs, FoldX (41), Mutabind (42) and BeAtMuSiC (43), all of which returned essentially random predictions (calculated correlations between predicted and measured binding affinity changes are 0.009, 0.017, and 0.032, respectively (FIG. 3)). These approaches were either unable to distinguish the differential effect of mutations on the two ligands (BeAtMuSiC), or if differences were detected these turned out not to correlate with the observations (FoldX, Mutabind). These results highlight the difficulty of predicting specificity-inducing mutations correctly and highlight the utility of the rs-pharmacophore-based approach described in this work in efficiently capturing these designs.

Discussion

The PD-1 signaling pathway is one of the inhibitory checkpoints that shapes T cell activity for anti-cancer (44) and anti-viral (45) immune responses (15, 44). Highly effective mAbs have been developed to disrupt both sides of the PD-1:PD-L1 interaction for the treatment of cancer (16, 17). As an alternative approach, a re-engineered PD1 with picomolar affinity to hPD-L1 was developed to block the wild type hPD-1:hPD-L1 interaction, with some possible advantages over conventional mAbs (25).

In this study, we utilized the ProtLID computational method (34) to re-engineer the protein binding interface of PD-1 for selective recognition of PD-L1, with the goal of introducing as few mutations as possible. ProtLID reduces the theoretical number of possible mutations to an experimentally manageable set using the concept of pharmacophore elaboration (46). The construction of a high-specificity interface to discriminate among multiple proteins with similar structure from the same superfamily, as in the current work, is highly challenging (47), in this case because PD-1 and its ligands share the same immunoglobulin fold. Interestingly, the most effective mutant designs of PD-1 to induce selectivity involved two residues (Y68 and T76), which interact with a highly conserved cluster of residues in PD-L1 and PD-L2. Retrospective structural analysis can explain the effect of these mutations, but these are hard to predict a priori.

TABLE 1

| human PD-L1/PD1 (4ZQK) | | | | mouse PD-L2/PD1 (3BP5) | | |
|---|---|---|---|---|---|---|
| Interface of hPD-L1 (4ZQK.A) | Interface of hPD1 (4ZQK.B) | rs-pharmacophore | designs | rs-pharmacophore | Interface of mPD1 (3BP5.A)* | Interface of mPD-L2 (3BP5.B) |
| PHE19 | LYS78 | HKNQRTW SEQ ID NO: 9 | K78R | HKNQW SEQ ID NO: 10 | LYS45(78) | PHE21 |
| ASP26 | GLN75, SER73 | HKNQRWY SEQ ID NO: 11 | Q75N, S73RK | HKNQRWY SEQ ID NO: 12 | GLN42(75), SER40(73) | GLU28 |
| TYR56 | ALA132, ILE134 | HIKLMNPQRVWY SEQ ID NO: 13 | I134QEDTNF SEQ ID NO: 14 | HNPQRSTWY SEQ ID NO: 15 | ALA99(132), ILE101(134) | GLN60 |
| GLN66 | ALA132, LYS131 | HKNPQRTWY SEQ ID NO: 16 | K131H | KNQRTWY SEQ ID NO: 17 | LYS100(133)# | SER67 |
| ARG113 | GLU136 | DEPQSY SEQ ID NO: 18 | E136QN | | | |
| MET115 | ILE126, LEU128 | FIMVWY SEQ ID NO: 19 | I126V, L128VMW | DFHIKLMNPQRSTVWY SEQ ID NO: 20 | ILE93(126), ALA92(125), ASN33(66), LYS45(78), GLY91(124), MET31(64)# | TRP110 |
| GLY120 | GLU84 | HPY | E84Y | | | |
| ALA121 | ASN66, LYS78 | KNQRSTWY SEQ ID NO: 21 | N66QE | | | |
| ASP122 | LYS78, TYR68 | HKNQRTWY SEQ ID NO: 22 | Y68KRNQ SEQ ID NO: 23 | HKNQRSWY SEQ ID NO: 24 | LYS45(78) | ASP111 |
| TYR123 | GLU136, GLY124, ILE126, ILE134, THR76, TYR68 | DEFHIKLM[1] NPQRTVWY[2] [1]SEQ ID NO: 25 [2]SEQ ID NO: 26 | I126V, T76DQENSY[1], G124VMY [1]SEQ ID NO: 27 | DEFHLMNP[1] QRSTVWY[2] [1]SEQ ID NO: 28 [2]SEQ ID NO: 29 | GLU103(136), ILE101(134), THR43(76), ASN35(68)# | TYR112 |

TABLE 1-continued

| human PD-L1/PD1 (4ZQK) | | | | mouse PD-L2/PD1 (3BP5) | | |
|---|---|---|---|---|---|---|
| Interface of hPD-L1 (4ZQK.A) | Interface of hPD1 (4ZQK.B) | rs-pharmacophore | designs | rs-pharmacophore | Interface of mPD1 (3BP5.A)* | Interface of mPD-L2 (3BP5.B) |
| LYS124 | ASP77, THR76 | DENPQSTY SEQ ID NO: 30 | D77E | DENQST SEQ ID NO: 31 | THR43(76) | LYS113 |
| ARG125 | GLN75 | HNPQSTW SEQ ID NO: 32 | | HIKLMNPQRSTVWY SEQ ID NO: 33 | ASN41(74), GLN42(75), GLU103(136), THR43(76) | TYR114 |

The first 3 columns list hPD-L1, hPD-1 residues in the interface and the corresponding rs-pharmacophore preferences for PD-L1. The last three columns show, in a similar fashion, the rs-pharmacophores for mPD-L2, and the structurally corresponding interface residues of mPD-1 and mPD-L2. The central column lists single residue mutants of hPD1 that were selected to induce PD-L1 specificity.

TABLE 2

| Mutation | AVE-hPD-L1 | AVE-hPD-L2 | STD-hPD-L1 | STD-hPD-L2 | t-statistics | Two-tailed p-value |
|---|---|---|---|---|---|---|
| Y68R | 0.876456405 | 0.033445075 | 0.008437621 | 0.010274871 | 141.781 | 1.89E−14 |
| Y68K | 0.774711472 | 0.022278096 | 0.008983203 | 0.018813393 | 80.7026 | 5.54E−10 |
| Y68N | 1.060521473 | 0.108439683 | 0.099555934 | 0.09135455 | 15.7559 | 2.84E−07 |
| T76D | 1.066772515 | 0.20528398 | 0.101702917 | 0.110906348 | 12.8015 | 1.40E−06 |
| Y68Q | 0.946517574 | 0.20176295 | 0.025207873 | 0.082775811 | 19.2458 | 1.12E−05 |
| K78R | 0.716545243 | 0.125063524 | 0.023788457 | 0.102307632 | 12.5917 | 0.000122932 |
| D77E | 0.956794794 | 1.125776788 | 0.038664958 | 0.040052918 | −6.78734 | 0.000140421 |
| T76E | 0.9640642 | 0.641683469 | 0.041368794 | 0.079282526 | 8.06098 | 0.000190529 |
| K131H | 0.994351458 | 1.579578832 | 0.092563067 | 0.155152673 | −7.24324 | 0.000238277 |
| Q75N | 0.969896594 | 1.129497843 | 0.022302473 | 0.050712945 | −6.44182 | 0.000937851 |
| N66Q | 0.361651172 | 0.010532588 | 0.113538667 | 0.004804627 | 6.90886 | 0.00227228 |
| I134N | 0.424420142 | 0.053442429 | 0.139751747 | 0.050837972 | 5.57813 | 0.00248728 |
| G124V | 0.960533228 | 1.157814602 | 0.029529666 | 0.09932396 | −4.2572 | 0.0092079 |
| S73R | 0.97075849 | 1.113224675 | 0.044996214 | 0.089809421 | −3.17134 | 0.019782 |
| I134F | 0.753900313 | 1.10854885 | 0.153483042 | 0.267588006 | −2.57072 | 0.0400823 |
| L128V | 0.881942986 | 1.027345791 | 0.024451683 | 0.112490036 | −2.82435 | 0.0429335 |
| L128W | 0.897043527 | 1.033264785 | 0.046812027 | 0.112337649 | −2.50286 | 0.0511656 |
| E136N | 0.889324374 | 0.820234238 | 0.043052541 | 0.054451187 | 2.2256 | 0.0584235 |
| E136Q | 0.861277766 | 0.967143216 | 0.074473749 | 0.079524797 | −2.17272 | 0.0617004 |
| I134Q | 0.097854454 | 0.025154896 | 0.065523381 | 0.028632223 | 2.27339 | 0.0675694 |
| G124M | 0.845121009 | 0.704707966 | 0.042961902 | 0.128279246 | 2.32087 | 0.0691911 |
| I126V | 0.862978279 | 0.710723533 | 0.059453802 | 0.146729984 | 2.15044 | 0.0812971 |
| T76S | 0.885344173 | 0.953666226 | 0.029152024 | 0.096908968 | −1.50963 | 0.194933 |
| T76N | 0.927660581 | 0.998189829 | 0.085646396 | 0.091255578 | −1.26014 | 0.243271 |
| G124Y | 0.650545997 | 0.557244172 | 0.128493079 | 0.186689237 | 0.920552 | 0.387512 |
| I134T | 0.378917311 | 0.306791314 | 0.117036032 | 0.147679228 | 0.855899 | 0.418209 |
| N66E | 0.006104358 | 0.004383021 | 0.004025551 | 0.003194503 | 0.748975 | 0.476389 |
| T76Y | 1.075411178 | 1.113595086 | 0.079905355 | 0.088057786 | −0.718051 | 0.493345 |
| S73K | 0.967521585 | 1.004199987 | 0.027082062 | 0.125564458 | −0.638492 | 0.555083 |
| I134D | 0.012970022 | 0.010518663 | 0.008740301 | 0.00639797 | 0.50605 | 0.627683 |
| T76Q | 0.957079559 | 0.980264494 | 0.058779294 | 0.094645654 | −0.465324 | 0.656474 |
| E84Y | 0.987208115 | 0.998721431 | 0.034309685 | 0.052567072 | −0.410121 | 0.694178 |
| Control | 0.014392837 | 0.006482458 | 0.007688471 | 0.004786447 | | |
| WT | 1 | 1 | 0 | 0 | | |

List of tested mutations of PD-1 (first column), five technical replicates of cell-assay-based experiments. The second and third column show average binding, normalized to wild type to PD-L1 and PD-L2. The fourth and fifth are the corresponding standard deviations. The sixth and seventh columns are the t-statistics and corresponding two-tailed p-values for differences in PD-1 binding affinity to PD-L1 and PD-L2.

REFERENCES

1. Lafferty K J & Cunningham A J (1975) A new analysis of allogeneic interactions. Aust J Exp Biol Med Sci 53(1): 27-42.
2. Chen L & Flies D B (2013) Molecular mechanisms of T cell co-stimulation and co-inhibition. Nat Rev Immunol 13(4):227-242.
3. Ishida Y, Agata Y, Shibahara K, & Honjo T (1992) Induced expression of PD-1, a novel member of the immunoglobulin gene superfamily, upon programmed cell death. EMBO J 11(11):3887-3895.
4. Dong H, Zhu G, Tamada K, & Chen L (1999) B7-H1, a third member of the B7 family, co-stimulates T-cell proliferation and interleukin-10 secretion. Nat Med 5(12): 1365-1369.
5. Latchman Y, et al. (2001) PD-L2 is a second ligand for PD-1 and inhibits T cell activation. Nat Immunol 2(3): 261-268.
6. Keir M E, Butte M J, Freeman G J, & Sharpe A H (2008) PD-1 and its ligands in tolerance and immunity. Annu Rev Immunol 26:677-704.
7. Chattopadhyay K, et al. (2009) Sequence, structure, function, immunity: structural genomics of costimulation. Immunological reviews 229(1):356-386.
8. Yamazaki T, et al. (2002) Expression of programmed death 1 ligands by murine T cells and APC. J Immunol 169(10):5538-5545.
9. Chemnitz J M, Parry R V, Nichols K E, June C H, & Riley J L (2004) SHP-1 and SHP-2 associate with immunoreceptor tyrosine-based switch motif of programmed death 1 upon primary human T cell stimulation, but only receptor ligation prevents T cell activation. J Immunol 173(2): 945-954.
10. Riella L V, Paterson A M, Sharpe A H, & Chandraker A (2012) Role of the PD-1 pathway in the immune response. Am J Transplant 12(10):2575-2587.
11. Wherry E J (2011) T cell exhaustion. Nat Immunol 12(6):492-499.
12. Sakuishi K, et al. (2010) Targeting Tim-3 and PD-1 pathways to reverse T cell exhaustion and restore anti-tumor immunity. J Exp Med 207(10):2187-2194.
13. Iwai Y, et al. (2002) Involvement of PD-L1 on tumor cells in the escape from host immune system and tumor immunotherapy by PD-L1 blockade. Proc Natl Acad Sci USA 99(19): 12293-12297.
14. Dong H, et al. (2002) Tumor-associated B7-H1 promotes T-cell apoptosis: a potential mechanism of immune evasion. Nat Med 8(8):793-800.
15. Nguyen L T & Ohashi P S (2015) Clinical blockade of PD1 and LAG3-potential mechanisms of action. Nat Rev Immunol 15(1):45-56.
16. Topalian S L, et al. (2012) Safety, activity, and immune correlates of anti-PD-1 antibody in cancer. N Engl J Med 366(26):2443-2454.
17. Brahmer J R, et al. (2012) Safety and activity of anti-PD-L1 antibody in patients with advanced cancer. N Engl J Med 366(26):2455-2465.
18. Postow M A, et al. (2015) Nivolumab and ipilimumab versus ipilimumab in untreated melanoma. N Engl J Med 372(21):2006-2017.
19. Lazar-Molnar E, et al. (2010) Programmed death-1 (PD-1)-deficient mice are extraordinarily sensitive to tuberculosis. Proc Natl Acad Sci USA 107(30):13402-13407.
20. Barber D L, et al. (2006) Restoring function in exhausted CD8 T cells during chronic viral infection. Nature 439 (7077):682-687.
21. Day C L, et al. (2006) PD-1 expression on HIV-specific T cells is associated with T-cell exhaustion and disease progression. Nature 443(7109):350-354.
22. Hoos A (2016) Development of immuno-oncology drugs—from CTLA4 to PD1 to the next generations. Nat Rev Drug Discov 15(4):235-247.
23. Fesnak A D, June C H, & Levine B L (2016) Engineered T cells: the promise and challenges of cancer immunotherapy. Nat Rev Cancer 16(9):566-581.
24. Lee C M & Tannock I F (2010) The distribution of the therapeutic monoclonal antibodies cetuximab and trastuzumab within solid tumors. BMC cancer 10:255.
25. Maute R L, et al. (2015) Engineering high-affinity PD-1 variants for optimized immunotherapy and immuno-PET imaging. Proc Natl Acad Sci USA 112(47):E6506-6514.
26. Lazar-Molnar E, et al. (2017) Structure-guided development of a high-affinity human Programmed Cell Death-1: Implications for tumor immunotherapy. EBioMedicine 17:30-44.
27. Mandell D J & Kortemme T (2009) Computer-aided design of functional protein interactions. Nat Chem Biol 5(11):797-807.
28. Lippow S M, Wittrup K D, & Tidor B (2007) Computational design of antibody-affinity improvement beyond in vivo maturation. Nat Biotechnol 25(10):1171-1176.
29. Kuhlman B, et al. (2003) Design of a novel globular protein fold with atomic-level accuracy. Science 302 (5649):1364.
30. Rothlisberger D, et al. (2008) Kemp elimination catalysts by computational enzyme design. Nature 453(7192): 190-195.
31. Looger L L, Dwyer M A, Smith J J, & Hellinga H W (2003) Computational design of receptor and sensor proteins with novel functions. Nature 423(6936):185.
32. Havranek J J & Harbury P B (2003) Automated design of specificity in molecular recognition. Nat Struct Biol 10(1):45-52.
33. Bolon D N, Grant R A, Baker T A, & Sauer R T (2005) Specificity versus stability in computational protein design. Proc Natl Acad Sci USA 102(36):12724-12729.
34. Yap E H & Fiser A (2016) ProtLID, a Residue-Based Pharmacophore Approach to Identify Cognate Protein Ligands in the Immunoglobulin Superfamily. Structure 24(12):2217-2226.
35. Zak K M, et al. (2015) Structure of the Complex of Human Programmed Death 1, PD-1, and Its Ligand PD-L1. Structure 23(12):2341-2348.
36. Lazar-Molnar E, et al. (2008) Crystal structure of the complex between programmed death-1 (PD-1) and its ligand PD-L2. P Natl Acad Sci USA 105(30):10483-10488.
37. Sali A & Blundell T L (1993) Comparative protein modelling by satisfaction of spatial restraints. J Mol Biol 234(3):779-815.
38. Holm L & Sander C (1995) Dali: a network tool for protein structure comparison. Trends Biochem.Sci. 20(11):478.
39. Sobolev V, Sorokine A, Prilusky J, Abola E E, & Edelman M (1999) Automated analysis of interatomic contacts in proteins. Bioinformatics 15(4):327-332.
40. Lundborg M & Lindahl E (2015) Automatic GROMACS topology generation and comparisons of force fields for solvation free energy calculations. J Phys Chem B 119 (3):810-823.
41. Schymkowitz J, et al. (2005) The FoldX web server: an online force field. Nucleic Acids Res 33(Web Server issue):W382-388.
42. Li M, Simonetti F L, Goncearenco A, & Panchenko A R (2016) MutaBind estimates and interprets the effects of sequence variants on protein-protein interactions. Nucleic Acids Res 44(W1):W494-501.
43. Dehouck Y, Kwasigroch J M, Rooman M, & Gilis D (2013) BeAtMuSiC: Prediction of changes in protein-protein binding affinity on mutations. Nucleic Acids Res 41(Web Server issue): W333-339.

44. Sznol M & Chen L (2013) Antagonist antibodies to PD-1 and B7-H1 (PD-L1) in the treatment of advanced human cancer-response. Clin Cancer Res 19(19):5542.
45. Gardiner D, et al. (2013) A randomized, double-blind, placebo-controlled assessment of BMS-936558, a fully human monoclonal antibody to programmed death-1 (PD-1), in patients with chronic hepatitis C virus infection. PLoS One 8(5):e63818.
46. Xu Z, et al. (2012) Affinity and cross-reactivity engineering of CTLA4-Ig to modulate T cell costimulation. J Immunol 189(9):4470-4477.
47. Schreiber G & Keating A E (2011) Protein binding specificity versus promiscuity. Curr Opin Struct Biol 21(1):50-61.
48. Rai B K, Madrid-Aliste C J, Fajardo J E, & Fiser A (2007) MMM: a sequence-to-structure alignment protocol. Bioinformatics 22(21):2691-2692.
49. Fernandez-Fuentes N, Madrid-Aliste C J, Rai B K, Fajardo J E, & Fiser A (2007) M4T: a comparative protein structure modeling server. Nucleic Acids Res 35(Web Server issue): W363-368.
50. Rai B K & Fiser A (2006) Multiple mapping method: a novel approach to the sequence-to-structure alignment problem in comparative protein structure modeling. Proteins 63(3):644-661.
51. Xu D & Zhang Y (2009) Generating triangulated macromolecular surfaces by Euclidean Distance Transform. PLoS One 4(12):e8140.
52. Case D A, et al. (2005) The Amber biomolecular simulation programs. J Comput Chem 26(16):1668-1688.
53. Ramagopal U A, et al. (2017) Structural basis for cancer immunotherapy by the first-in-class checkpoint inhibitor ipilimumab. Proceedings of the National Academy of Sciences of the United States of America 114(21):E4223-E4232.

What is claimed is:

1. A human Programmed Cell Death-1 (PD-1) receptor mutant comprising at least the first 149 consecutive amino acids of SEQ ID NO:1 with mutation Y68R or Y68K, wherein the mutant has selectivity for PD-LI compared to PD-L2 and wherein the mutant has undetectable PD-L2 binding.

2. A fusion polypeptide comprising the PD-1 receptor mutant of claim 1 fused to an immunoglobulin domain polypeptide.

3. The fusion polypeptide of claim 2, wherein the mutant is fused to the immunoglobulin domain polypeptide by a peptide bond between a terminal amino acid of the mutant and a terminal amino acid of the immunoglobulin domain polypeptide.

4. The fusion polypeptide of claim 2, wherein the immunoglobulin domain polypeptide comprises an immunoglobulin IgG1 Fc domain.

5. The fusion polypeptide of claim 4, wherein the immunoglobulin IgG1 Fc domain is human.

6. A composition comprising the PD-1 receptor mutant of claim 4, and a pharmaceutically acceptable carrier.

7. The PD-1 receptor mutant of claim 1 further comprising a radiolabel.

8. A method of imaging a PD-L1 positive tumor in a subject comprising administering the radiolabeled PD-1 receptor mutant of claim 7 to the subject, where the mutant binds to the tumor, and imaging the radiolabeled mutant bound to the tumor.

9. A method of stimulating T cell activation, treating a tumor, or treating an infection in a subject comprising administering to the subject a human Programmed Cell Death-1 (PD-1) receptor mutant comprising at least the first 149 consecutive amino acids of SEQ ID NO: 1 with mutation Y68R or Y68K, wherein the mutant has selectivity for PD-LI compared to PD-L2 and wherein the mutant has undetectable PD-L2 binding, or a fusion polypeptide comprising the PD-1 receptor mutant fused to an immunoglobulin domain polypeptide, or a composition comprising the PD-1 receptor mutant or the fusion polypeptide, in an amount effective to stimulate T cell activation, treat a tumor, or treat an infection, respectively, in a subject.

10. The method of claim 9, wherein the T cell activation comprises cytokine secretion.

11. The method of claim 9, wherein the subject has a tumor.

12. The method of claim 9, wherein the subject has an infection.

\* \* \* \* \*